United States Patent [19]
Vijil-Rosales

[11] Patent Number: 4,781,189
[45] Date of Patent: Nov. 1, 1988

[54] PNEUMATIC EXSANGUINATOR AND METHOD FOR EXSANGUINATING A LIMB

[76] Inventor: Cesar A. Vijil-Rosales, 5642 Indigo, Houston, Tex. 77096

[21] Appl. No.: 794,242

[22] Filed: Nov. 1, 1985

[51] Int. Cl.⁴ .............................................. A61B 17/12
[52] U.S. Cl. ............................ 128/327; 128/DIG. 20
[58] Field of Search ...... 128/325, 327, 1 D, DIG. 20, 128/60

[56] References Cited

U.S. PATENT DOCUMENTS

| | | | |
|---|---|---|---|
| 3,279,459 | 10/1966 | Schenker | 128/327 |
| 4,066,084 | 1/1978 | Tillander | 128/327 |
| 4,465,076 | 8/1984 | Sturgeon | 128/327 |
| 4,566,436 | 1/1986 | Loefquist | 128/327 |

FOREIGN PATENT DOCUMENTS 817521 7/1959 United Kingdom ................. 128/60

OTHER PUBLICATIONS

Basic Circulatory Physiology, Components of the Circulation, Daniel R. Richardson, 1976 1st Ed., Little, Brown and Company, Boston, pp. 12-13.
Campbell's Operative Orthopaedics, Sixth Edition, Edmonson and Crenshaw Editors, pp. 113-115, 117-118.
Anaesthesia for Orthopaedic Patients, by Alan Loach, pp. 11-14.
Regional Block of the Upper and Lower Extremity by Intravenous Injection of a Local Anaesthetic Solution, Regional Block, Dr. Moore, Charles C. Thomas Publisher, pp. 307-318.

Primary Examiner—John D. Yasko
Attorney, Agent, or Firm—Vaden, Eickenroht, Thompson & Boulware

[57] ABSTRACT

A device and method for exsanguinating a limb using at least one inflatable bladder which surrounds the extremity of the body to be exsanguinated. The bladder is inflated at the distal end of the limb applying pressure which causes the blood to be evacuated from the limb while monitoring the applied pressure. The limb is exsanguinated and prepared for surgery under sterile and controlled conditions.

7 Claims, 2 Drawing Sheets

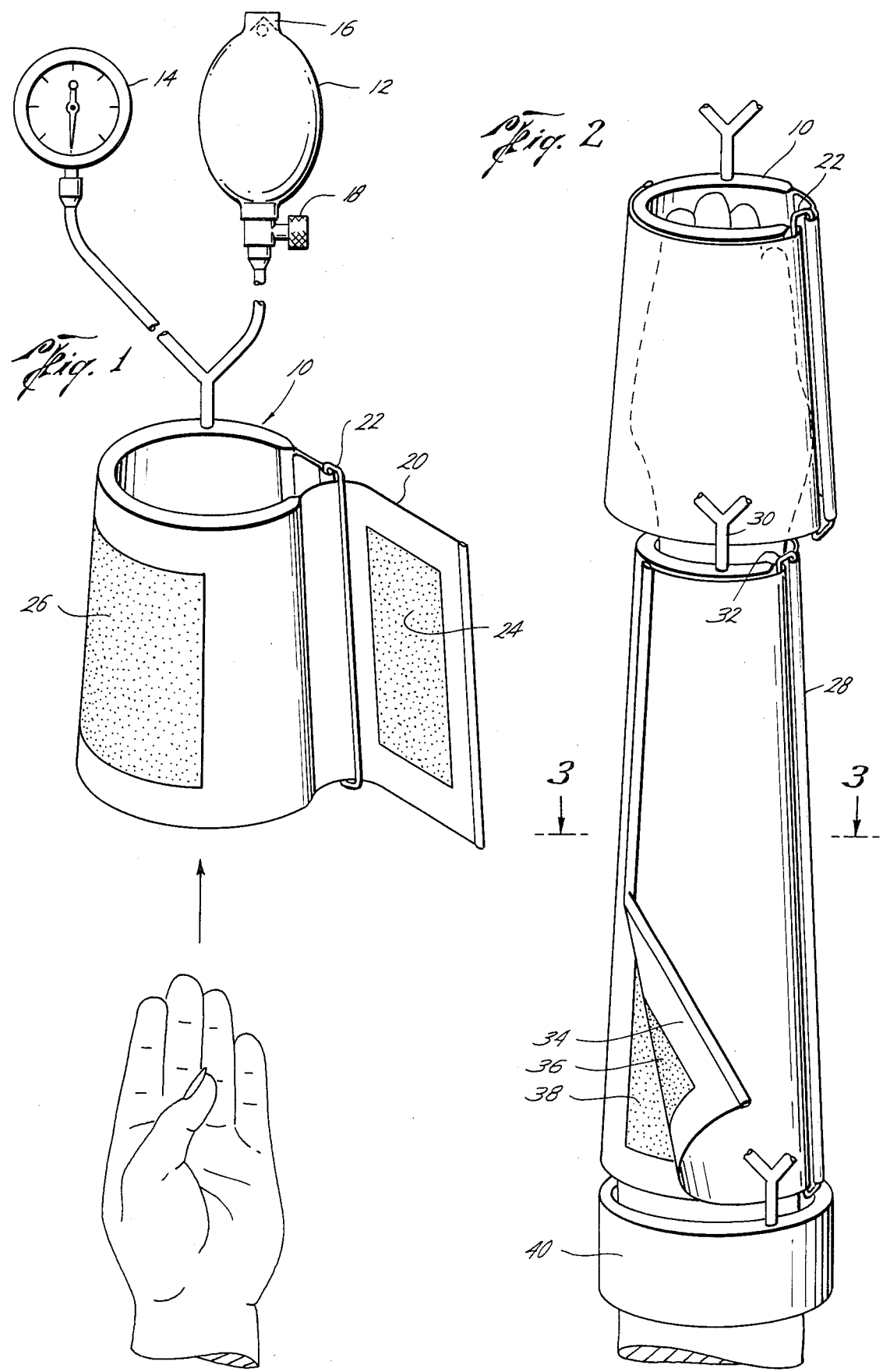

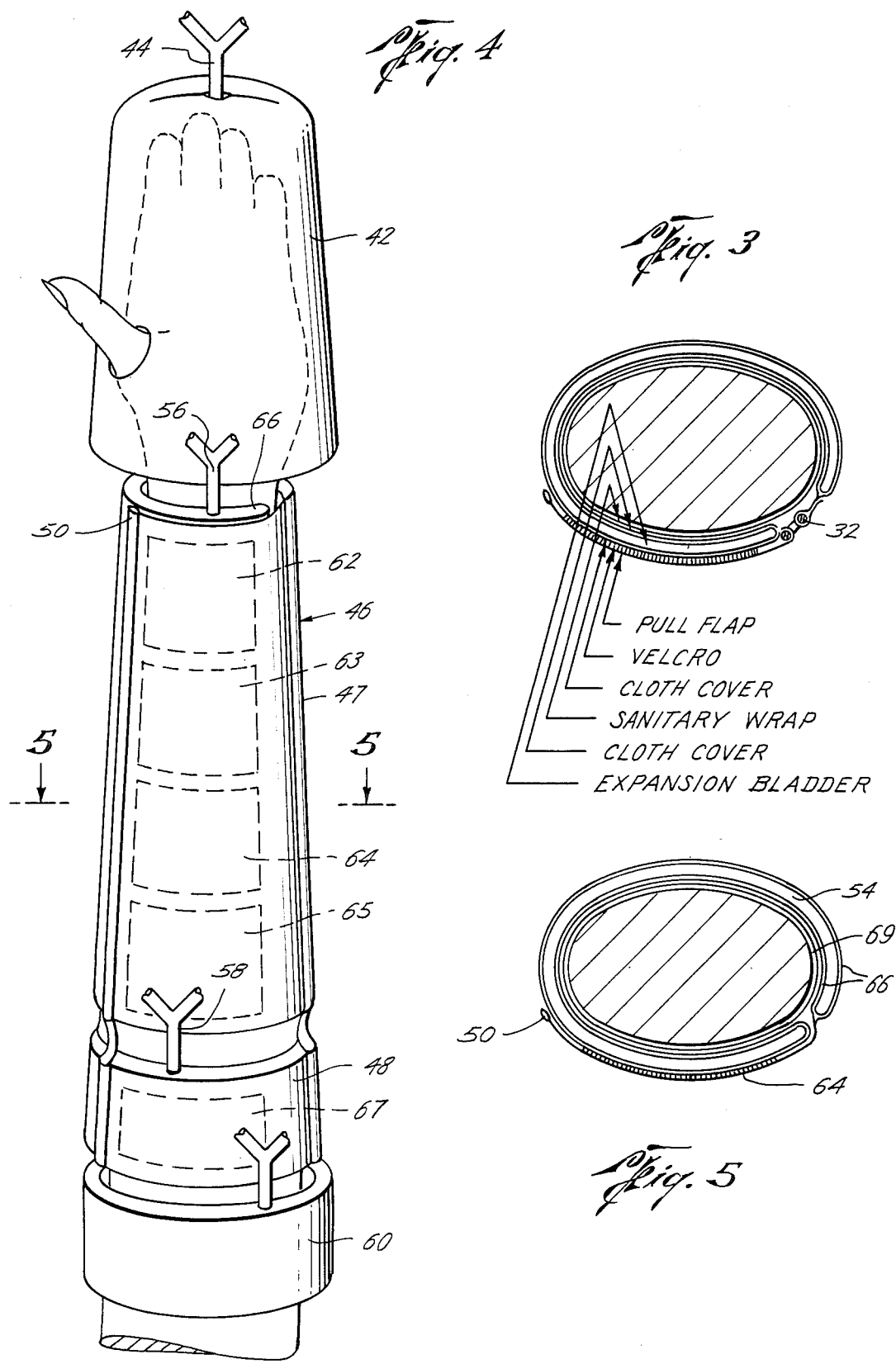

PNEUMATIC EXSANGUINATOR AND METHOD FOR EXSANGUINATING A LIMB

BRIEF DESCRIPTION OF THE INVENTION

The device and method of this invention relate to an improvement in the exsanguination (blood removal) of an extremity or limb to be prepared for surgery. During arm or leg surgery, particularly with the advent of microsurgery, the tissue must be as bloodless as possible. A pneumatic inflatable bladder is enclosed or encased in a fabric covering in the size and shape to insert a hand or foot. The fabric covering confines the bladder which will be inflated during exsanguination and provides a shape and pattern for the extremity or limb to be inserted. The bladder is inflated in a similar manner to the tourniquet of a pneumatic cuff with a manometer to monitor the pressure and pressure bulb to pump up the bladder.

The exsanguinator shaped for the hand is used with one or more separate exsanguinators for the arm. An exsanguinator with one or more bladders or chambers to be inflated is placed around the arm. At the proximal end of the limb to be exsanguinated, a separate chamber or bladder can be placed as a backup to the usual tourniquet which is in place during surgery to prevent blood flow into the limb. This arrangement is used to exsanguinate a limb prior to surgery and includes a series of pneumatic inflatable bladders starting at the extremity either the hand or the foot. Additional exsanguinators are wrapped around the limb progressively from the distal end to the point where the tourniquet is placed. The exsanguination system can also be used for exsanguination of a limb in preparation of use of a regional intravenous nerve block anesthetic.

In preparing the limb for surgery, the exsanguinator on the extremity is inflated to the desired pressure. Next, the exsanguinator proximate to the extremity likewise is pressurized to evacuate the blood from the limb. The series of exsanguinators used are pressurized from the distal to the proximal end of the limb. Then the tourniquet is pressurized to maintain the exsanguinated state during surgery. The exsanguinator on the extremity subject to the surgical procedure is removed after sufficient pressure for exsanguination. However, the other exsanguinators on the limb can remain in place after they have been inflated for exsanguination and subsequently deflated if they do not interfere with surgery. In the event that additional exsanguination of the limb is desired for any reason, the exsanguinators are in place to be re-inflated. During the entire exsanguination procedure of this invention, precise measurements of the pressures used and time intervals can be recorded.

BACKGROUND OF THE INVENTION

In orthopedic surgery involving an extremity, a bloodless field is desirable. Microsurgery continues to increase and a bloodless field is even more important for this type of fine work. The typically used practice is to elevate the limb so that as much blood as possible drains by gravity. Then an elastic or gum rubber bandage of the Esmarch or Martin type is used to exsanguinate the hand or foot. The bandages which are two to four inches wide are wrapped in a spiral around the extremity to squeeze out the blood at a tightness determined by the physician or assistant preparing the extremity. There is no way to determine the pressure being applied to the extremity. Also, the wrapping takes some period of time to wind the bandage in an overlapping spiral around the extremity. The manipulation of the arm or leg during the wrapping can impart additional distress on an injury in the case of post-accident surgery.

The various texts on orthopedic anesthesia recognize this type of exsanguination with a bandage as the state of the art method. See *Campbell's Operative Orthopaedics*, (Sixth Ed.) Edmonson and Crenshaw Eds. pp. 113-115; and *Anesthesia for Orthopaedic Patients* by Alan Loach, pp. 11-14. The preferred tourniquet is a pneumatic cuff and the texts describe improvements in this type of tourniquet since pressure can be monitored and maintained at a certain desired level. Timing devices and alarms can be used with the pneumatic cuff. The pneumatic cuff is usually operated by a pressure line in the hospital or a cylinder of compressed gas. The tourniquet pressure is applied after the limb is wrapped and is inflated to a pressure higher than systolic arterial pressure for the arm. The texts devote considerable discussion to the length of time a tourniquet can be used safely and the damage to nerves and vessel which can occur as well as ischemic tissue damage.

For operations lasting more than 1 to 1½ hours, the tourniquet needs to be released to avoid damage and the wrapping procedure is repeated. When the tourniquet is released after or during surgery, there is a dramatic increase in blood flow. This causes hyperaemia which is relieved by compression dressing and elevation of the limb. A complete exsanguination as possible is also necessary for a regional block of an extremity for intravenous injection of local anesthesia. The proper dosage of anesthesia will be diluted by residual blood fluid in the extremity if exsanguination is not complete. The use of the local anesthetic without the ability to determine the proper dosage is undesirable.

Great concern is placed on the preparation and monitoring of the limbs which are isolated and exsanguinated for surgery. The tourniquet usage has been improved, but the initial exsanguination of the limb prior to tourniquet inflation to maintain the bloodless state is rather primitive bandage wrapping with no measurable controls on the pressure applied.

SUMMARY OF THE INVENTION

This invention relates to the exsanguination of a limb under controlled conditions. The procedure can be performed quickly and will avoid as much additional trauma to a damaged limb. The exsanguinator for the hand and arm is a series of controlled pneumatic bladders that are fashioned to include a mitt or tapered cylinder to insert the hand and tapered cylindrical sleeves to insert the arm. The exsanguinators have a fabric cover which can be fastened tightly around the hand and arm and contain an inflatable bladder connected to a pump and manometer. The hand exsanguinator is inflated first to evacuate blood from the hand then the arm exsanguinator is pressurized from the distal to the proximal and to the desired pressure. In the case of the arm, the exsanguinator can have multiple chambers which are inflated from distal to proximal end.

Similar exsanguination procedure can be performed on the foot. This would require a boot-like enclosure for the foot which would have at least one expandable bladder which can be inflated. Sleeves to fit the leg would be used. A series of as many exsanguinator sleeves to go up the leg as necessary can be used. It is not intended to limit the invention to any particular number or shape or form of exsanguinators to be used on the various size or type of limb.

The devices and method to practice this invention give the medical team a way to monitor the pressure exerted on an extremity or the limb during exsanguination before the tourniquet is inflated. The controlled measure of the pressure will give a more reliable and consistent degree of exsanguination. After exsanguination, the extremity to be operated on can be exposed while the other exsanguinators on the limb may be left in place and deflated or, if necessary, pressure may be maintained at desired level during the surgical procedure.

The devices and method provide a time saving technique for exsanguination when quickness is needed for emergency surgery. Also, there is less trauma to the injured limb or hand which is not subject to the manipulation necessary for a spiral wrap. There will be less pain and damage for the patient. The devices can be sterilized and made of disposable material.

The exsanguinator and method of this invention is also beneficial to a complete exsanguination that is needed for regional intravenous block of local anesthetic. The arm or leg can be exsanguinated under controlled conditions for a more complete exsanguination. The anesthetic will be introduced into the extremity without dilution by blood to give more reliable results on deadening the operative site.

Another advantage of the exsanguinator and method is its use during prolonged surgery when a repeated exsanguination is necessary. If surgery progresses past a certain time interval the limb may need circulation of blood to prevent tissue damage. At this time the tourniquet is released to allow circulation. To continue the operation after circulation of the blood the limb can be raised to permit as much fluid to drain from the operative site. The limb exsanguinators which do not interfere with the operative site can be reapplied and pressurized. This achieves a better exsanguination than just applying the tourniquet.

A limb exsanguinator placed close to the tourniquet and left in place during surgery can be an emergency backup if the tourniquet fails. The exsanguinator or the chamber closest to the tourniquet can be manually inflated to some point above the arterial systolic pressure. This feature is helpful because there can be a failure in hospital pressure lines or other problems with the tourniquet and the medical team can quickly prevent circulation into the limb.

In addition to using the exsanguinator for surgical preparation of a limb, it can be used for intravenous injection for patients who have veins that are difficult to locate. A partial exsanguination of the arm is performed. After the pressure is released, there is a marked increase of blood flow into the arm and the veins are easier to locate.

DESCRIPTION OF THE DRAWINGS

FIG. 1 shows a hand to be inserted into somewhat tapered cylindrical hand exsanguinator with pressure bulb and manometer.

FIG. 2 shows the hand inserted into the hand exsanguinator and single chamber limb exsanguinator and tourniquet.

FIG. 3 shows a cross-section of the exsanguinator of FIG. 2.

FIG. 4 shows an alternative embodiment of a hand exsanguinator in the form of a mitt and limb exsanguinator with two chambers and an additional separate limb exsanguinator.

FIG. 5 shows a cross-section of the exsanguinator at line 5 of FIG. 3.

FIG. 6 shows a foot exsanguinator in open configuration.

FIG. 7 shows a foot exsanguinator surrounding a foot.

DESCRIPTION OF THE PREFERRED EMBODIMENTS

Several illustrations of hand and arm exsanguinators of this invention are shown in the Figures. The presentation in the Figures is illustrative of the shapes that the exsanguinator can take. The illustrations are not intended to limit the shapes and forms which can be desired to exsanguinate the desired limb.

As shown in FIG. 1 hand with the thumb folded in the palm is sterilized and prepared for exsanguination. At this point the hand and limb ordinarily would be wrapped with a bandage in a spiral manner without a way to monitor pressure of the bandage used for the wrap. The hand and limb can be placed in a sterile, thin disposable bag or wrap (not shown) prior to insertion into the hand exsanguinator 10. The hand exsanguinator 10 is a tapered cylindrical shape when wrapped around the hand with an inside diameter large enough to hold the hand. The hand exsanguinator 10 prior to wrapping around the hand is a generally trapezoid shape when laid flat. The hand exsanguinator 10 covers the hand and fingers as shown in FIG. 2.

At the distal end of the hand exsanguinator 10 is a pressure bulb 12 which is used to inflate the exsanguinator. Manometer 14 is used to monitor the pressure exerted. The pressure bulb 12 is similar to those used on pneumatic cuffs and has a check valve 16 to introduce air into the bulb 12 and a pressure relief valve 18 used to deflate the exsanguinator. Although a pressure bulb arrangement is shown, any type of mechanism to introduce and relieve pressure can be used. The pressure mechanism is preferred to be placed at the distal end of the hand so that to the extent possible pressure travels from the distal to the proximal end of the limb.

In the embodiment of FIGS. 1 and 2, the exsanguinator is fastened around the hand by inserting fabric flap 20 through buckle 22. The fabric flap 20 has a Velcro patch 24 which attaches to a Velcro patch 26 on the outside of the exsanguinator 10 to provide a snug fit around the hand. Any type of fasteners or snapping mechanism can be used to insure a secure fit around the hand.

FIG. 2 shows a hand in the exsanguinator prepared for exsanguination. A sleeve-type exsanguinator 28 for the arm forms a tapered cylinder from the wrist covering the elbow with appropriate inside diameters for enclosing the limb. The sleeve exsanguinator 28 when unbuckled and laid flat is a generally elongated trapezoid shaped fabric which encloses at least one bladder. The smaller end encircles the wrist and the larger end encircles the upper part of the arm. The sleeve exsanguinator can have one or more chambers for inflation. In FIG. 2, a one chamber arm exsanguinator is shown with the tubing connection 30 indicating the pressure bulb and manometer which are not shown. The pressure bulb is placed at the point closest to the hand so that to the extent possible, the pressure exerted on the arm starts at the wrist and extends proximally past the elbow.

A buckle 32 which extends the length of arm exsanguinator receives a pull flap of fabric 34 which is pulled through the buckle 32 to give the pull desired snug fit around the arm. Fabric flap 34 does not surround the bladder as shown in FIG. 3. Pull flap 34 has a length of Velcro patch 36 incorporated into the flap which corresponds to Velcro patch 38 on the outside of the arm exsanguinator. The Velcro patches fasten the arm exsanguinator in place. As stated previously, any type of fastener can be used for placement and fitting the exsanguinator on the arm.

FIG. 3 shows a cross-section of the arm exsanguinator which is typical of the internal arrangement of the exsanguinators of this invention. An expansion bladder of rubber or other inflatable material is in the center. The bladder is shaped to conform with type of exsanguinator. For the arm, the bladder is generally a long trapezoid shape when the arm exsanguinator is laid flat before fastening around the arm. When the arm exsanguinator is in place, the bladder surrounds the arm. The hand exsanguinator 10 has a similarly shaped but smaller less elongated bladder. The bladder is connected by tubing to a pressure bulb and manometer (not shown in FIG. 3) which is used to pump air into the bladder to inflate the bladder around the limb to be exsanguinated. In FIG. 3, the exsanguinator is shown in the fastened position around the limb with the bladder encircling the limb. The bladder is encased in a durable fabric or cloth cover that will confine the room for expansion of the bladder. The cloth cover has a pull flap with a Velcro patch that fastens with Velcro patch on the outside of the exsanguinator. As the bladder is inflated, the cloth cover does not expand appreciably and maintains the shape of the exsanguinator. There is enough room for expansion of the bladder to exert the desired pressure on the limb. FIG. 3 also shows a sanitary wrap which can be placed on the limb for sterile purposes prior to placement of the exsanguinator.

The tourniquet 40 that is typically used for surgical procedures is shown in FIG. 3. The tourniquet is generally placed above the elbow during arm surgery. In FIG. 3, the hand can be exsanguinated first at a controlled and measured pressure. Then the arm is exsanguinated against a controlled and measured pressure. Next, the tourniquet is inflated to maintain pressure above arterial systolic pressure during surgery. The arm exsanguinator can be left in place if it is out of the field of surgery. The arm exsanguinator is deflated after the tourniquet pressure is applied. If it is necessary for recirculation into the arm, the tourniquet is released and blood flows into the arm. Then the arm exsanguinator is inflated at the desired pressure and the tourniquet is pressurized repeating the steps for the initial exsanguination.

The exsanguinator of this invention can be used with regional block intravenous injections of anesthetic solution. Before exsanguination a needle or catheter is placed in the vein. The exsanguinator is carefully placed over the needle or catheter and inflated. The anesthetic is not injected until after exsanguination and the tourniquet is in place.

FIG. 4 shows another type of hand exsanguinator 42 in the shape of a mitt with the thumb exposed. The fabric cover would be generally truncated conical mitt shape with a hole for the thumb and enclose one or more inflatable bladders. The thumb has relatively small amount of blood from exsanguination standpoint. The tubing connection 44 to the pressure bulb and manometer is shown at the distal end. A multi-chamber arm exsanguinator 46 is shown in FIG. 5 with a separate larger exsanguination chamber 47 and smaller exsanguination chamber 48 used in series to illustrate some of the variations of the invention. Arm exsanguinator 46 is fastened by Velcro patches without the use of a buckle. To accommodate different arm sizes the Velcro patches 62, 63, 64 and 65 are provided on the larger chamber 47 to encircle the exsanguinator around varying diameters of the limb. The smaller chamber 48 has one Velcro patch 67.

Cloth flap 50 overlaps the outside of the portion of the exsanguinator which contains the bladder and the facing patches of Velcro holding the arm exsanguinator 46 in place. The multi-chamber exsanguinator 48 has two inflatable bladders inside the cloth cover in chambers 47 and 48. Each bladder has separate tube connections 56 and 58 for separate inflation. In practice, the hand would be exsanguinated then the large bladder in chamber 47 closest to the hand is inflated to exsanguinate the wrist and part of the arm next to the hand. Next the smaller bladder in chamber 48 is inflated. In FIG. 4, the smaller chamber 48 which is used to exsanguinate the distal portion of the arm acts as a backup to tourniquet 60.

FIG. 5 shows a cross-section through one of the chamber of the multi-chamber arm exsanguinator 46. The bladder 54 is shown encircling the arm. The Velcro fastening patches 62 which face each other are shown with cloth flap 50 in the overlapping position. The sanitary wrap 69 for sterilization also encircles the arm. The cloth cover 66 encases the bladder 54 and functions to shape the exsanguinator and provide the necessary restraint for inflation of the bladder as previously described. The encasement material can be any durable fabric or material which can enclose the bladder and provide a smooth surface to contact the limb.

FIG. 6 is the opened foot exsanguinator 70 which is made as described above with fabric encased bladders 72 and 74. Also shown are tubing connections 76 and 78 which connect to the pneumatic bulb and manometer. FIG. 7 shows the foot exsanguinator 70 surrounding a foot with bladder 72 around the foot and bladder 74 around the lower leg and ankle adjacent to the foot.

The sleeve-type exsanguinator 28 in FIG. 2 and the multi-chamber arm exsanguinator 46 shown in FIG. 5 can be used to prepare a patient for intravenous injection. This is particularly helpful and practical for example with those patients with hard to locate veins that are deep or in obese patients. The arm exsanguinator is put in place as shown in FIGS. 2 and 3 and inflated for about 5 minutes which partially exsanguinates the arm. The pressure is released and marked increase of blood into the arm occurs. The usual pneumatic tourniquet is applied as shown in FIGS. 2 and 3. With the increased blood flow into the arm, the vein is more prominent and easier to locate for intravenous injection. The use of the exsanguinator for a partial exsanguination to aid in intravenous use is a practical application of this method to eliminate the probing with an i.v. needle without penetration of the vein which caused bruising and discomfort to the patient. Although the exsanguinator used for illustration purposes in FIGS. 2 and 3 is for the arm it is not intended that only the arm can be treated for partial exsanguination to expose a vein for intravenous injection. Any limb section can be partially exsanguinated with an appropriately sized pneumatic exsanguinator.

From the foregoing it will be seen that this invention is one well adapted to attain all of the ends and objects hereinabove set forth, together with other advantages which are obvious and which are inherent to the method.

What is claimed is:

1. A method for exsanguinating a limb comprising the steps of:
   encircling the limb with multiple means for pneumatic compression, multiple means to release pressure, and multiple means to monitor the pressure, each of said multiple means operating independent of each other;
   compressing the limb first with the compression means nearest the extremity of the limb and sequentially compressing the independent compression means to the proximal end of the limb while monitoring independently the pressure in each compression means; and
   exsanguinating said limb with the exertion of the independently monitored pressure in each of the compression means.

2. A limb exsanguinator system comprising:
   an encasement material sized to be adapted to surround at least a part of a limb to be exsanguinated;
   at least two inflatable bladders enclosed in said encasement material and adjacent to each other in said encasement material;
   means for securing said encasement material around the limb with each of said bladders encircling said limb to be exsanguinated;
   separate means for inflating each of said bladders;
   separate means to monitor the pressure therein of each of said bladders; and
   separate means for releasing the pressure therein of each of said bladders.

3. A limb exsanguinator system of claim 2 wherein said encasement material is a fabric.

4. A limb exsanguinator system of claim 2 wherein said means securing said encasement material around the limb is a series of Velcro ® patches spaced along the encasement material which correspond to interact and fasten when the encasement material surrounds the limb.

5. A foot and leg exsanguinator system comprising:
   an encasement material sized and adapted to surround the foot and extend upward to surround at least part of the leg;
   at least two inflatable bladders enclosed in said encasement material;
   means for securing said encasement material around the foot and leg;
   one of said bladders in a generally trapezoidal shape adapted to surround the foot to be exsanguinated;
   at least one additional bladder adjacent to the trapezoidal bladder which generally is rectangular and is adapted to surround the leg;
   a separate means for inflating each of said bladders;
   separate means to monitor the pressure therein of each of said bladders; and
   separate means for releasing the pressure therein of each of said bladders.

6. A foot and leg exsanguinator of claim 5 wherein said encasement material is a fabric.

7. A foot and leg exsanguinator of claim 5 wherein said means securing said encasement material is a series of Velcro patches spaced along the encasement material which correspond to interact and fasten when the encasement material surrounds the foot and leg.

* * * * *